US006961586B2

(12) United States Patent
Barbosa et al.

(10) Patent No.: US 6,961,586 B2
(45) Date of Patent: Nov. 1, 2005

(54) FIELD ASSESSMENTS USING HANDHELD DATA MANAGEMENT DEVICES

(75) Inventors: Frank A. Barbosa, Carrollton, TX (US); Luis M. Ortiz, Dallas, TX (US)

(73) Assignee: Field Data Management Solutions, LLC, Albuquerque, NM (US)

( * ) Notice: Subject to any disclaimer, the term of this patent is extended or adjusted under 35 U.S.C. 154(b) by 392 days.

(21) Appl. No.: 09/955,543

(22) Filed: Sep. 17, 2001

(65) Prior Publication Data

US 2004/0192329 A1 Sep. 30, 2004

Related U.S. Application Data

(60) Provisional application No. 60/233,120, filed on Sep. 18, 2000.

(51) Int. Cl.[7] .............................................. H04M 1/00
(52) U.S. Cl. ............................... 455/556.1; 455/566.2; 455/90.3; 705/2
(58) Field of Search .................... 455/556.1, 556.2, 455/66.1, 90.1, 90.2, 90.3; 705/1, 2

(56) References Cited

U.S. PATENT DOCUMENTS

| | | | | |
|---|---|---|---|---|
| 5,444,615 A | * | 8/1995 | Bennett et al. ................. | 705/8 |
| 5,561,446 A | * | 10/1996 | Montlick .................... | 345/173 |
| 5,990,932 A | * | 11/1999 | Bee et al. ................. | 348/14.08 |
| 6,064,968 A | * | 5/2000 | Schanz .......................... | 705/1 |
| 6,083,353 A | * | 7/2000 | Alexander, Jr. ............. | 202/158 |
| 6,172,620 B1 | * | 1/2001 | Brick et al. ................... | 341/22 |
| 6,650,647 B1 | * | 11/2003 | Ishikawa et al. ............ | 370/400 |
| 6,662,193 B1 | * | 12/2003 | Christensen ............. | 707/104.1 |

FOREIGN PATENT DOCUMENTS

JP  408055161 A  *  2/1996  ........... G06F 17/60

* cited by examiner

*Primary Examiner*—Melur Ramakrishnaiah

(57) ABSTRACT

Systems for and methods of conducting field assessments utilizing handheld data management devices are diclosed. Methods and systems for executing field assessments use handheld devices provide assessors portable access to industry-specific programs and data useful in carrying out a field assessment. Field assessment data synchronization and/or delivery is enabled using wireless capabilities resident in handheld personal computing devices. Data may be synchronized with a server over a network using wireless radio transmission, or directly to a computer workstation using wireless infrared or radio transmission or connected means (e.g., modems, cradles, docking stations). It is another aspect of the present invention to provide for two-way communication between remote computing means (e.g., servers, desktop computers) and handheld data management devices to facilitate real-time access to remote programs, assistance and/or information related to the field assessment being undertaken by using a handheld data management device user.

32 Claims, 9 Drawing Sheets

FIELD ASSESSMENTS USING HANDHELD DATA MANAGEMENT DEVICES

This application claims priority to Provisional Patent Application, Ser. No. 60/233,120, entitled "Field Assessment Using Handheld Data management Devices," filed Sep. 18, 2000.

FIELD OF THE INVENTION

The present invention is generally related to applications for handheld data management devices (e.g., personal digital assistants, handled computers, two-way pagers, Web/WAP-enabled telephony, etc.). More particularly, the present invention is related to systems for and methods of conducting field assessments utilizing handheld data management devices.

BACKGROUND

One problem with growth and demand for services in many of the professions, trades and industries wherein field assessments, estimates or appraisals are required is that less experienced personal may be undertaking the initial tasks of data collection and, sometimes, the analysis and troubleshooting of problems in the field. Field personnel are usually required to collect facts regarding a situation in the field that may later be used by more senior, experienced and/or responsible personnel to make decisions (business, technical, administrative and/or political). Even the most experienced professionals may find themselves lacking access to critical information or support that would be helpful in undertaking field operations.

Individuals in the construction industry, for example, are often responsible for carrying out field assessments and estimates. The consequences of under bidding a project in the construction field may be very costly and/or may affect performance and quality of services/activities related to the underbid project. In cases where a project cost estimate, or bid, must be provided for a construction project, a business owner or senior journeymen may oftentimes be compelled to personally go the field and collect information regarding a project in order to render a realistic and profitable bid because an inexperienced estimators may render inaccurate appraisals. Construction project estimates require an accurate assessment and analysis of a job site/projects in order to develop the data/facts necessary for an estimate to be rendered regarding use of labor, materials and completion time for a project.

If a field estimator was provided with guidance, access to supplemental information and/or years of experience (e.g., lessons learned by senior personnel), field operations may proceed more accurately and professionally. A field estimator, however, is unlikely to have reasonable means to efficiently access the information or the information may not be updated. Materials typically used in the field may include reference materials such as codes, regulations and price lists.

Personal digital assistant (PDA) is the generic name used for a device belonging to a family of portable handheld data managing devices well known in the art. Currently, handheld data management devices such as PDAs or Palm PCs can have as much computing power as some desktop personal computers and have been used in a wide variety of applications, including wireless communication (infrared and radio frequency), GPS (global positioning system) mapping, Internet access and database storage. Web-phones are also being introduced to the wireless marketplace that have PDA-like capabilities.

Handheld data management devices are generally enabled with connectivity to data sources over, for example, the connection-oriented Transmission Control Protocol/Internet Protocol (TCP/IP) or message oriented TME/X protocol. Cellular Digital Packet Data (CDPD) is a TCP/IP based technology that supports Point-to-Point Protocol (PPP) or Serial Line Internet Protocol (SLIP) wireless connections to mobile devices. Cellular service is generally available throughout the world from major service providers. With CDPD, data can be transferred over switched PSTN circuits or packet-switched networks. Currently, CDPD supports data transmissions up to 19.2 Kbps. Global System for Mobile Communication (GSM) and Personal Communications Systems (PCS) networks operate in the 800 MHz, 900 MHz, and 1990 MHz range, PCS provides narrowband digital communications in the 900 MHz range for paging, and broadband digital communications in the 1900 MHz band for cellular telephone service. In the U.S., PCS 1900 is identical to GSM 1900. GSM operates in the 900 MHz, 1800–1900 MHz frequency bands. GSM 1800 is widely used throughout Europe and throughout many parts of the world. In the U.S., GSM 1900 is the same as PCS 1900; thus, these two technologies are compatible. Currently, GSM networks support data speeds up to 9.6 Kbps. The Code Division Multiple Access (CDMA) network is a digital wireless network that defines how a single channel can be segmented into multiple channels using a pseudo random signal (or code) to identify each user's information. Because CDMA spread each call over more than 4.4 trillion channels across the entire frequency band, it is more immune to interference than TDMA or other current wireless networks and can support more users per channel in some situations. Time Division Multiple Access (TDMA) cellular/wireless system are currently deployed throughout the wireless communication markets. Currently, some networks support data at speeds up to 14.4 Kbps. Wideband CDMA (W-CDMA), which is called CDMA 2000 in North America, will be implemented in the U.S.A in the near future. W-CDMA is a true 3G wireless technology. W-CDMA increases transfer rates by using multiple 1.25 MHz cellular channels compared to the single channel currently used by CDMA 1.

The General Packet Radio Service (GPRS) network is a 2.5G technology that bridges the gap between the current wireless technologies and the next generation of wireless technologies known as 3G wireless technologies. GPRS is a packet-data transmission technology that will initially provide data transfer rates up to 115 Kbps. GPRS will work with CDMA and TDMA, and it supports X.25 and IP communications protocols. It will also enable features like Voice over IP (VOIP) and multimedia services. BlueTooth is a Personal Area Network (PAN) technology. Adopted by a consortium of wireless equipment manufacturers called the BlueTooth Special Interest Group (BSIG), it is emerging as a global standard for low cost wireless data and voice communication. The current specification for this standard is the 2.4 GHz ISM frequency band.

BlueTooth technology is based on a short-range radio transmitter/receiver built into small application specific circuits (ASICs) and embedded into support devices. Initially, BlueTooth enabled devices will have 1 mw of transmitter power and will be capable of asymmetrical data transfers of up to 721 Mbps over distances of 10M. The BlueTooth specification permits up to 100 mw of power, which will increase the range to 100M. In addition, it can support up to three voice channels. Using short data packets and frequency hopping of up to 1600 hops per second, it is a true 3G wireless technology that will enable a host of new applications and possibilities for wireless data communication. Wireless application protocol (WAP) and Extensible Markup Language (XML) are examples of current technology being used in wireless devices and system to provide Web-based (Internet) content on wireless devices.

Despite the growing power and popularity of portable data management devices and the diverse telecommunications alternatives for data communication, few applications are available today that directly relate to interactive or industry-specific programs providing management of associated data and providing users with access to daily business practices and procedures related to a particular industry.

What is apparently needed in industries requiring field assessments is access to industry-specific information and/or support that may enable field assessors, estimators, investigators and the like to more efficiently and accurate render field assessments.

SUMMARY OF THE INVENTION

It is an object of the present invention to provide methods for executing field assessments using handheld devices.

It is an aspect of the present invention to provide assessors portable access to industry-specific programs and data useful in carrying out a field assessment.

It is another aspect of the present invention provides a handheld data management device and solutions for assisting personnel in conducting field assessments.

It is another aspect of the present invention to provide methods for field assessment data synchronization and/or delivery using wireless capabilities resident in handheld personal computing devices. Data may be synchronized with a server over a network using wireless radio transmission, or directly to a computer workstation using wireless infrared or radio transmission or connected means (e.g., modems, cradles, docking stations).

It is another aspect of the present invention to provide for two-way communication between remote computing means (e.g., servers, desktop computers) and handheld data management devices to facilitate real-time access to remote programs, assistance and/or information related to the field assessment being undertaken by using a handheld data management device user.

A handheld data management device for field assessments can include a memory for storing field assessment programs and related data; microprocessor for executing field assessment programs; field assessment software stored within said memory; user interface for enabling a user to interact with said field assessment software; and sychronization means for providing data to and retrieving data from remote computing resources. The systems and devices may also include a field assessment program module for analyzing input data associated with a field assessment, analyzing said data, and rendering output data in response to said input data and said analyzing; a positioning module, for providing handheld device location identification; and a wireless communication module for providing access to remote data resources to said device.

A programming module containing field assessment software may include software used to accomplish at least one of:
construction industry analysis;
HVAC analysis;
project management;
equipment readiness;
troubleshooting;
inventory tracking;
inventory ordering;
legal investigation;
multi-users function coordination.

A method of conducting a field assessment using a handheld data management device can include the steps of providing access to a industry-specific field assessment program module; executing said program module to conduct a field assessment; providing field-specific information required by said program module for said program module to render data from said module useful in support of said assessment; and retrieving data from said handheld data management device in support of said assessment. The method may further include providing data to a remote resource for analysis, and retrieving enhanced data from said remote resource for use in conducting the field assessment.

A method of conducting a assessment of a field problem by an assessor utilizing a handheld data management device, may also include the steps of obtaining direction to a field problem using positioning and navigation means provided through said handheld data management device; starting an assessment program associated with the field problem; providing specific information required by the assessment program and related to the field problem; analysis of said specific information by said handheld data management device; and rendering output by said handheld data management device for use in support of said field problem.

The foregoing has outlined some of the more pertinent features of the present invention. These features should be construed to be merely illustrative of some of the more prominent features and applications of the invention. Many other beneficial results can be attained by applying the disclosed invention in a different manner or modifying the invention as will be described. Accordingly, other aspects and a fuller understanding of the invention may be had by referring to the following Detailed Description of the preferred embodiment.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF PREFERRED EMBODIMENTS

The present invention now is described more fully hereinafter with reference to the accompanying drawings, in which preferred embodiments of the invention are shown. Like numbers refer to like elements throughout. This invention may, however, be embodied in many different forms and should not be construed as limited to the embodiments set forth herein; rather, these embodiments are provided so that this disclosure will be thorough and complete, and will fully convey the scope of the invention to those skilled in the art. Aspects of the present invention are directed to assisting people in the field with rendering accurate assessments of a situation, job, environment, project, etc. Reference to a particular field environment (e.g., projects within the construction industry) made throughout the description are provided for exemplary purposes only and should not be taken as a limitation of the present invention. The present invention provides portable, handheld data management devices (e.g., handheld or palm computer/PC, PDA, mobile telephony devices) with access to industry/profession-specific processes and applications to enable users to be more productive in field assessments.

Figure 1:
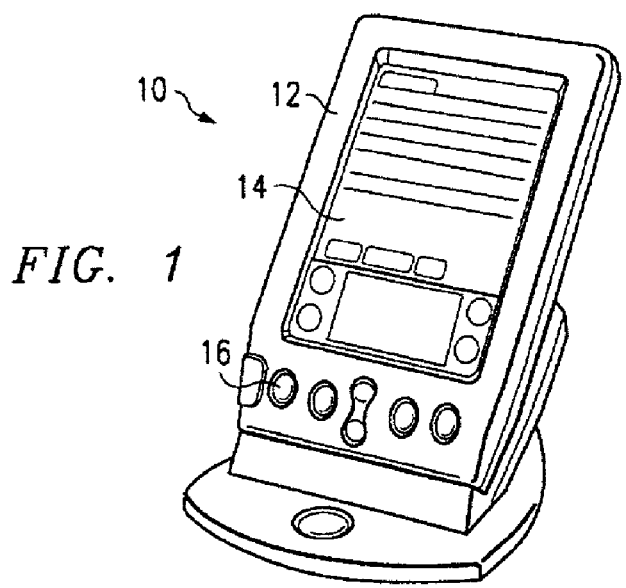
FIG. 1 is a perspective view of a portable electronic device usable in accordance with carrying of methods of the present invention.

A handheld data management device in accordance with the present invention may be in the form of any one of a number of commercially available hand-held devices such as personal digital assistants (PDAs), two-way pagers, and Web/WAP-enabled mobile phones. Referring to FIG. 1, a device 10 exemplary of a prior art PDA that could implement software and/or communication methods in accordance with carrying out methods of the invention is illustrated. The device 10 includes an outer housing 12 sufficiently small to be easily portable such that it substantially fit within the palm of a users hand, a display 14 that may also preferably include touch-screen technology to operate in combination with control buttons 16 to provide a User Interface (UI) for operating, controlling and/or otherwise interacting with the device 10. Not shown on the device 10, but well known in the art to be incorporated in such devices are communication ports (wired and wireless).

Figure 2:
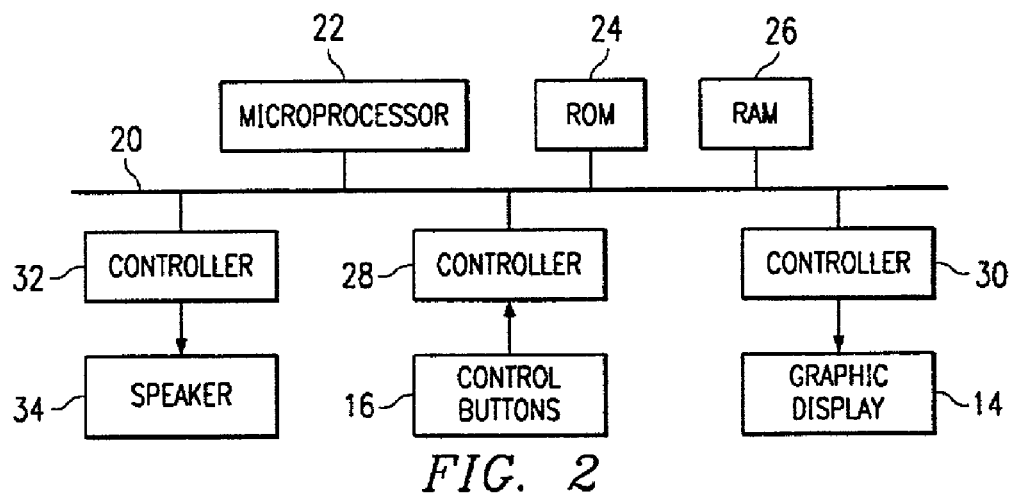
FIG. 2 is a block diagram of various components of the device.
Figure 3:
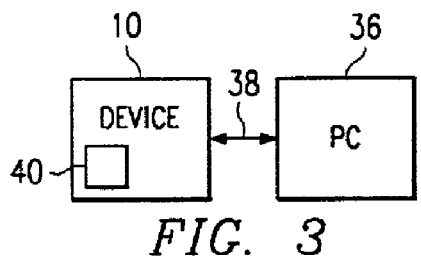
FIG. 3 is a block diagram of a device including a communication module to facilitate communication of the device.

FIG. 2 is a block diagram of various components of the device 10. The device 10 includes a system bus or plurality of system buses 20 to which various resident components are coupled and by which communication between the various components is accomplished. A processor 22 is connected to the system bus 20 and is supported by a read only memory (ROM) 24 and a random access memory (RAM) 26. The ROM 24 contains among other code the code controlling basic hardware operations. The RAM 26 is the main memory into which the operating system and application programs are loaded. Also connected to this system bus 20 are various I/O controllers, including a controller 28 providing the hardware interface for the control buttons 16, and a controller 30 providing the hardware interface for the display 14. A controller 32 provides the hardware interface for a speaker 34. One of the preferred implementations of the invention is as a set of instructions in a code module resident in the RAM 26 of the device. The set of instructions may however be stored in some other computer memory such as a hard disk drive of a personal computer (PC) or even downloaded from a server via the Internet until required by the device 10. As shown in FIG. 3, the device 10 may also include an integrated communication module 42 to facilitate wired and wireless communication. Communication may be had with remote resources 44 (e.g., servers) through network and to enable monitoring and feedback of field assessment operations. Wireless communication module 42 may include digital communication technology and/or wireless modem for facilitating local area communication. The module 46 also preferably uses wireless IP technology, which is also known as Cellular Digital Packet Data (CDPD). CDPD is a method of transmitting data in small packets of information over existing cellular phone networks. CDPD is a fully digital network overlay, providing all the benefits of digital service, including lower error rates and lower costs. or cellular-based communications. Communications module 42 provides wireless real-time access to servers and personnel in support of assessments, and may also provide more traditional information available over networks, (e.g., e-mail, chat, Intranet and Internet information). Preferably, no plugging in or dialing up in needed through integration of the communication module 42 into a handheld device.

Figure 4:
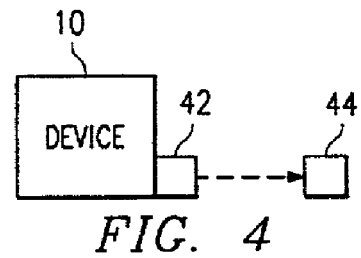
FIG. 4 is a block diagram showing an infrared communications link between the device and a personal computer.

As shown in FIG. 4, the device 10 can preferably communicate with a PC 36 through an infrared communications link 38 to exchange and update information both ways. This feature makes it particularly easy to update and change personal schedules as needed. The device 10 may include an integrated modem 40 to provide data transfer functions and for remote connectivity. This feature allows a person (such as a supervisor, counselor or service representative) remote from the user to provide tasks, answers to queries, notes and other information for use and display on the users device 10 using standard telecommunications technology (e.g.,wired and wireless GSM, CDMA, CDPD, and paging networks).

Figure 5:
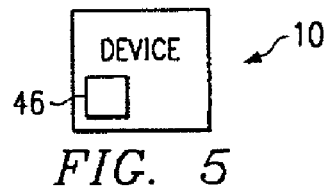
FIG. 5 is a block diagram showing a GPS module associated with the device.

Referring to FIG. 5, the handheld device may also be equipped within a position module 46 to enable the handheld device to utilize positioning systems or methods known in the art such as satellite position (e.g., Global Positioning System (GPS)) or signal triangulation techniques. A GPS compatible system, for example, may be used to determine a device location information and may also provide navigational assistance to users (e.g., to find a field problem/job) when used in combination with navigation software or resources, such as the Mapblast.com (TM) resource available from the World Wide Web. A navigation module will include positioning and navigational capabilities. Commercially available navigation technology will allows users to download a door-to-door route from any two locations in the U.S. The device will constantly update the user's current position and provide updated directions. This feature allows point to point navigational instructions to be provided to the users.

In accordance with the present invention, a handheld device 10 may be interactive with the field assessor when programs operated by the microprocessor ask questions or provide guidance related to a particular field problem. An interactive question and answer session may also include the provision of checklists and relevant data in support of a user dialogue with the device. Interactivity may also be provided to remote resources when two-way communication is provided between the device and a remote server and/or support representative. As mentioned above, the present invention may be effectively practiced together with a client/server programming environment. As is known by those skilled in this art, client/server is a model for a relationship between two computer programs in which one program, the client, makes a service request from another program, the server, which fulfills the request. Although the client/server model can be used by programs within a single computer, it is more commonly used in a network where computing functions and data can more efficiently be distributed among many client and server programs at different network locations. With a client/server relationship, multiple client programs share the services of a common server. Client programs and Server programs are often part of a larger program or application. Relative to the Internet, a Web browser is a client program that requests services (the sending of Web pages or files) from a Web server (which technically is called a Hypertext Transport Protocol or HTTP server) in another computer somewhere on the Internet. Similarly, a computer with TCP/IP installed allows client requests for files from File Transfer Protocol (FTP) servers in other computers on the Internet.

Figure 6:
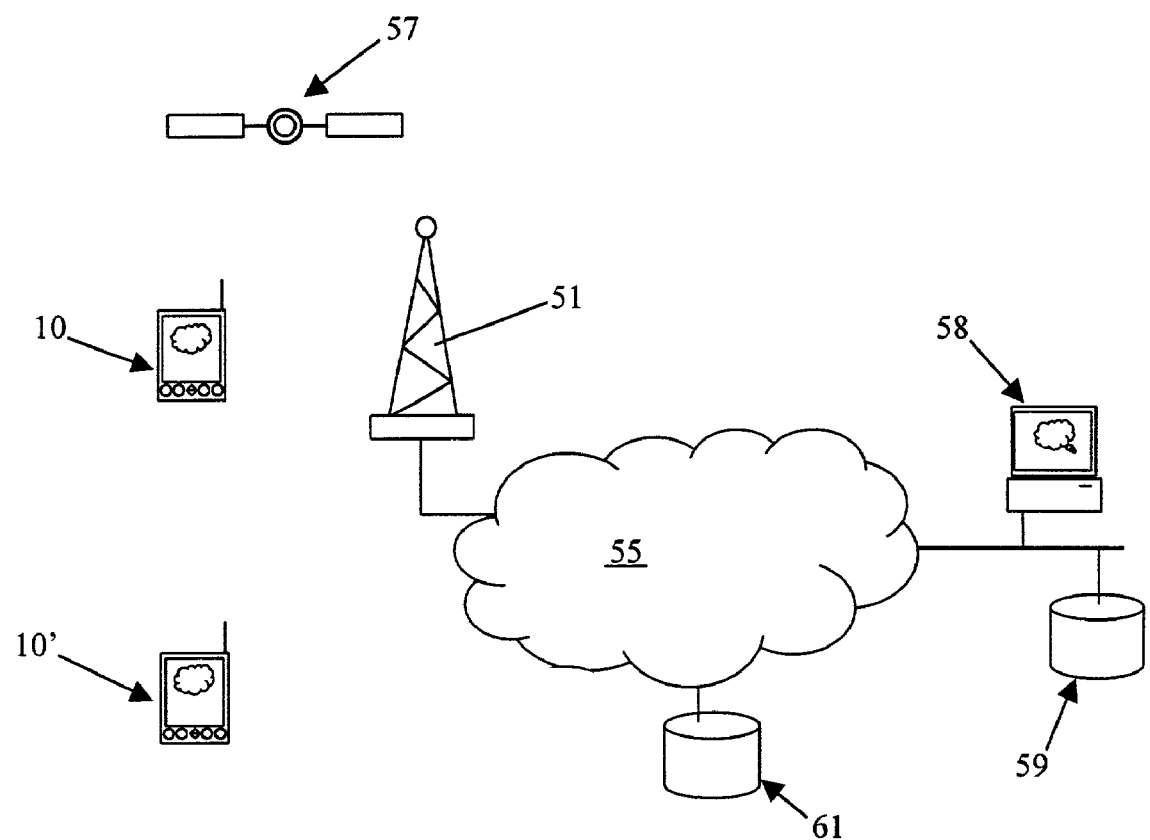
FIG. 6 an illustration of a basic operational environment for the handheld device and methods of the present invention.

Referring to FIG. 6, an environment for extended operation/communication between a handheld device 10 (client) and remote management system 58 (e.g., server, desktop PC) is illustrated. At least one device 10/10' can be remotely linked to a management system that may provide templates (e.g., task/punch lists) and/or programs to a group of users. A template may be stored locally on a user's personal digital assistant (PDA). Job templates and/or programs may also be centrally stored within one or more databases 61/59 accessible to management system or the directly by the a handheld device 10/10'. Accordingly, users may access a central template through a private or public computer networks in a conventional manner via wireline or wireless communications. By maintaining a template in a central location, such as a management system, updates can be made to the template as procedures, best practices, and/or laws are added, amended or deleted. Accordingly, users can be provided with up-to-date information on assessment activities.

A user in the field may utilize a handheld device 10 for assessment of a field problem. The user can execute a industry-specific program on the handheld device 10 related to the problem being addressed. The user interacts with the handheld executed program to obtain an initial field assessment. The program would prompt the user for input of data related to the problem. During program execution, the user may access remote resources (e.g., information, data, assistance) via wireless communication systems 51 and networks 55. Information may be obtained from a server 58 located at the user's enterprise, or from other network 55 resources available to the user (e.g., Web pages provided/obtained over the Internet). Realtime analysis of data obtained may also be undertaken by remote processor (e.g., server, desktop PC). At completion of data processing by a handheld device remote processor 10 a final output, such as a report, bid, recommendation, or the like may be provided to the user. The user may use the information to counsel a third party, render a final output for the third party, or to troubleshoot equipment. The remote processor (e.g., 58) may also be used as a collection point for data provided from multiple users (e.g., 10, 10'). The data would then be analyzed by the remote processor and a comprehensive report may result remote user/device location and data can also be provided via satellite 57. Location is determinable using, for example, GPS. A handheld device user may be provided with directions to a requested location, based on the user's position, either textually or through known mapping programs (e.g., MapBlast(TM)).

It should be appreciated that data collected with the device 10 may be processed without the assistance of remote resources and can be directly utilized to render output to the user via the device UI, printed using data rendering devices, or may be stored in local memory for subsequent use (e.g., synchronization with a desktop, rendering, remote computation, compilation for use with input from other sources).

Data provided to remote systems can generally undergo computing operations beyond the resident capabilities of the handheld device. A limited software program may be used for gathering of data during a field assessment, where after a larger software application and computing resources may be necessary to render a comprehensive analysis relating to the particular field problem. A smaller handheld executed program, for example, may only provide a device user with a more abbreviated list of questions needed to address a field problem. For example, a larger computing capability may utilize data collected by several handheld devices deployed to assess field problems.

Methods of the present invention are now described more fully hereinafter with reference to the accompanying drawings, in which preferred embodiments of the invention are shown. Methods of the invention may, however, be embodied in many different forms and should not be construed as limited to the embodiments (e.g., method step sequences) set forth herein; rather, these embodiments are provided so that this disclosure will be thorough and complete, and will fully convey the scope of the invention to those skilled in the art. It will be understood after the teachings herein provided that each block of the flowchart illustrations, and combinations of blocks in the flowchart illustrations, can be implemented by computer program instructions. These computer program instructions may be provided to a processor of a handheld device (e.g., PDA, pager, WAP phone), general purpose computer (e.g., desktop), special purpose computer (e.g., server), or other programmable data processing apparatus to produce a machine, such that the instructions, which execute via the processor of the handheld device, remote computer, server or other programmable data processing apparatus, create means for implementing the functions specified in the flowchart block or blocks. It is generally known that servers or desktop computers have more processing capability than handheld device. Furthermore, a server or desktop may be used as a centralized data collection and analysis facility for input received from more than one handheld device/user.

Figure 7:
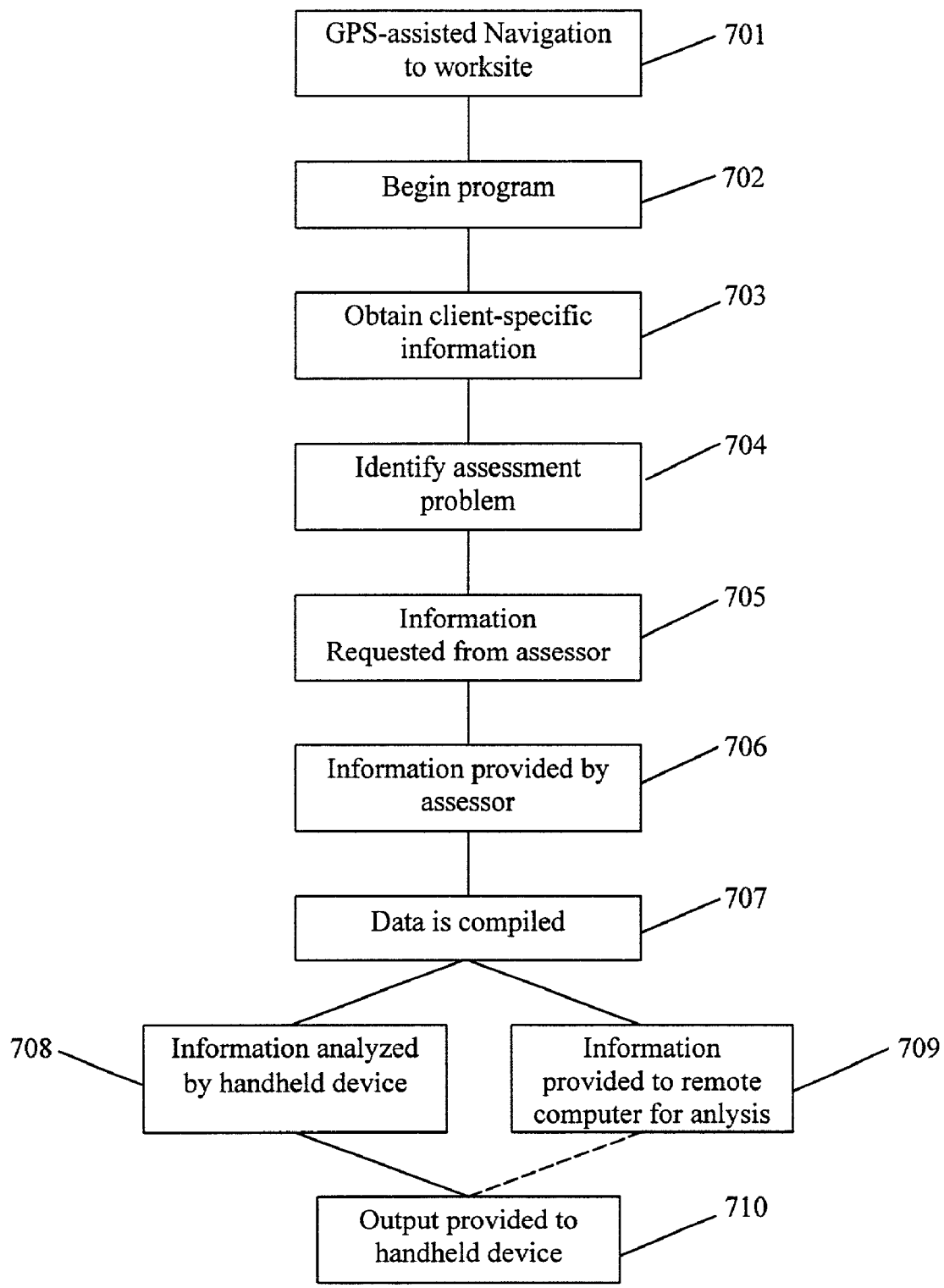
FIG. 7 illustrates a flow chart related to a construction industry in accordances with a method of the present invention.

Referring to FIG. 7, a flow chart related to a construction industry application will now be described. An assessor may initially be directed to the prospective job site 701 through GPS navigation means on the handheld device relevant to a particular field problem. Once at the job site, the assessor would start the an appraisal program 702. The program may start by asking for the identification of a the client or matter 703 (e.g., customer, or job site). The program may next ask the representative to identify the problem or type of assessment 704 (e.g., HVAC, plumbing, electrical, landscaping, etc.). This should enable the only the most relevant questions and/or interaction to be invoked by the program. The program would then start asking the user specific questions, or provide initial information, related to the identified subject matter 705. The user would respond to program questions by providing specific answers/data 706, which would generally be provided in a format understandable by the program. It is assumed that assessors/users would have the requisite training to utilize assessment programs. Interaction, however, would preferably be kept to a level that is reasonably intuitive to any reasonably experienced computer and handheld device user. At completion of the series of questions, the handheld device may automatically compile collected data 707 provided by user. The data may then be analyzed by the handheld device 708 or provided the data to a remote processor 709 via a network where the data will be analyzed. Data may be provided to the remote resource within a template recognizable by the remote processor/program. After the data is analyzed, the handheld device may provide output to the assessor 710 (which may have been received from the remote processor) that can be in the form of an estimate or analysis and may be provided to the client or utilized by the assessor to provide additional services.

In a industry-specific application, a field assessor in the construction industry may be required to provide job estimates, status reports and/or complete a punch list of items. Programs for estimating a job and rendering bids may be more detailed and interactive than the mere provision of task/punch lists. For example, a job estimation program tailored for the heating and air conditioning industry may determine cooling load requirements based on data collected regarding a floor plan (square footage, duct work, number of vents, position of vents), currently used equipment (furnace, air compressor, valves, coil, tubing, etc.), condition of equipment and insulation. Load calculations may also be rendered on-site based on available building plans where input to program questions is based on data written on a set of architectural plans. In the heating and air conditioning (HVAC) industry for example, an inexperienced technician would greatly benefit from the provision of guidelines for troubleshooting HVAC equipment, such as a series of questions related to identified failure symptoms or the identified problem. The handheld device may also provide a technician with an outline of known systematic procedures.

In the case where an inexperienced assessor, such as the inexperienced HVAC technician described above, is unable to properly assess a field problem, a transcript of the assessor's interaction with the handheld (e.g., questions and responses) may be transmitted to remote resources for further analysis. The assessor may be provided, at the handheld device with additional assessment guidelines (e.g., another program, suggestions/advice, or targeted questions not asked by the handheld device program) from a remote processor or source. The assessor may also be provided with, for example, a link to third party information relevant to the problem available on the Internet (e.g., information from an equipment manufacturer's site regarding the equipment being assessed by the technician).

Figure 8:
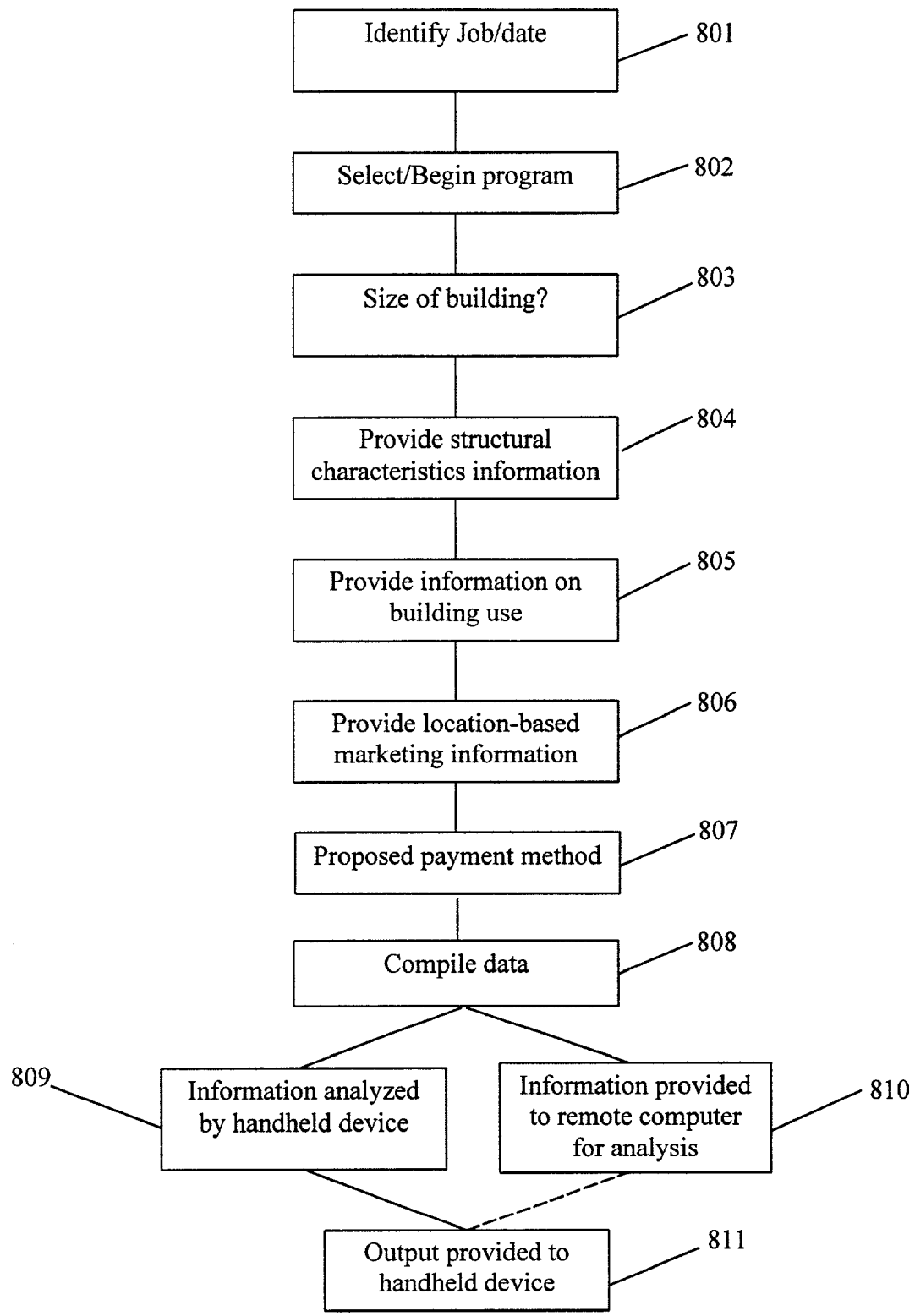
FIG. 8 illustrates a flow chart illustrating a more specific assessment relating to the HVAC industry.

Referring to FIG. 8, a detailed flow chart illustrating a more specific assessment relating to the HVAC industry is described. The flow chart is directed to information useful in obtaining data needed to render an estimate for a HVAC project. Once a program is opened on the handheld device, the assessor may be asked (e.g., prompted) to identify the job 801 (e.g., location, customer name, date, type of job). The current date may already be available from the handheld device, but in this case the projected start date may be provided for project scheduling (conflict checking) purposes. The assessor may then select the type of program 802 to be utilized (e.g., HVAC Estimating, trouble-shooting, efficiency assessment). The assessor may next be asked for the approximate size of the building 803 being assessed (generally based on heated/cooled square footage for HVAC applications). A assessor may then be asked to provide structural characteristics of the building 804 (e.g., glass-type and location, the direction a building faces for determining solar exposure, ceiling height and ceiling type). Other categories not shown but which may be relevant to assessing a building are wall type, insulation type/rating, duct work type/insulation, pre-existing equipment type/rating. Use of the building may also be determined by the assessor 805 (e.g., how the building occupied and typical traffic patterns). The type of business, if applicable, may have an impact on the assessment regarding accessibility for equipment and commercial operation patterns. Finally, location (e.g., Dallas/Fort Worth factor) may have an impact on the market price for an estimate. It may make a difference whether a job is being performed in a particular part of town or what the immediate surroundings of the property are like. Project location information may be provided by the handheld device automatically via a resident GPS module as described in FIG. 5 and throughout the disclosure; however, location-based marketing information 806 (e.g., street access, landscaping that may be disturbed, new construction issues) may also impact the project and overall assessment. Payment information 807 may also be obtained to complete information needed to render, for example, a job estimate. Compilation 808, analysis 809/810, and useful output 811 aspects of the method are carried out and rendered after all data is collected by the assessor. Other construction related fields that would benefit from a series of questions similar to the last example include, remodeling, plumbing, inspections, surveying, landscaping, windows sales and installation, floor covering contractors, etc. It should be appreciated that estimates may also be provided in non-construction fields using the present method.

Figure 9:
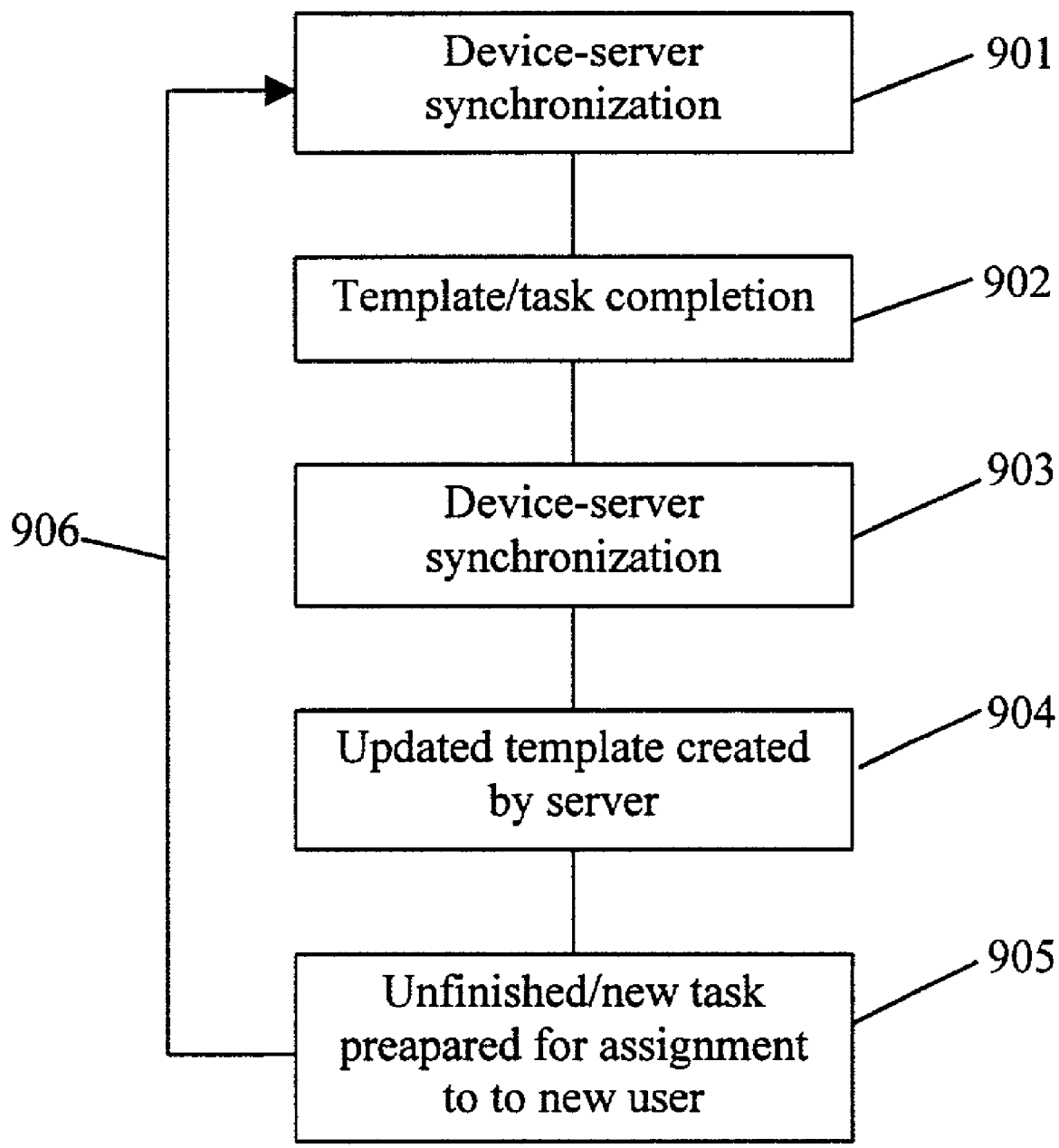
FIG. 9 illustrates a flow chart of a method relating to project management.

Referring to FIG. 9, a flow chart a method relating to project management is described. Oftentimes, large projects in, for example, a manufacturing or design environment may have job aspect that are shared by members belonging to different work shifts. In accordance with the present invention, a program managed by a central computer/server may track every aspect of a project and provide worker with tasks via a template. A worker's handheld device (or device assigned to the worker for the shift) may be synchronized 901 with a server to receive an updated template containing tasks for the worker at the beginning of every work shift. A project member beginning a workday at a job site or on a shared project would generally be expected to ascertain the status of the project and attempt to complete tasks embodied within a template. The projects tasks and template are generally expected to be completed by the worker 902 during and before the end of a shift. The worker reports 903 on the status of tasks at the end of the workday via synchronization with a server through wired and/or wireless means as described at the beginning of the disclosure. An updated template is created by the server 904 for a subsequent worker based on the project's updated status, needs and prior worker input. Unfinished business recorded by a prior worker and new tasks may be prepared within a template 905 for provision to the subsequent device/worker. The process is repeated for the duration of assigned projects 906, and for subsequent (new) projects. It is an advantage of the present invention to provide for project tracking, updated progress, and focused task lists to projects members. Project efficiency would increase with the present method. Workers utilizing a synchronized project task list to carry out their daily input into a project can insure that task completed task are not repeated (wasting time) and that unfinished task are addressed by a subsequent project member, possibly avoiding project delays and/or damages (e.g., monetary loss based on inefficiency).

Figure 10:
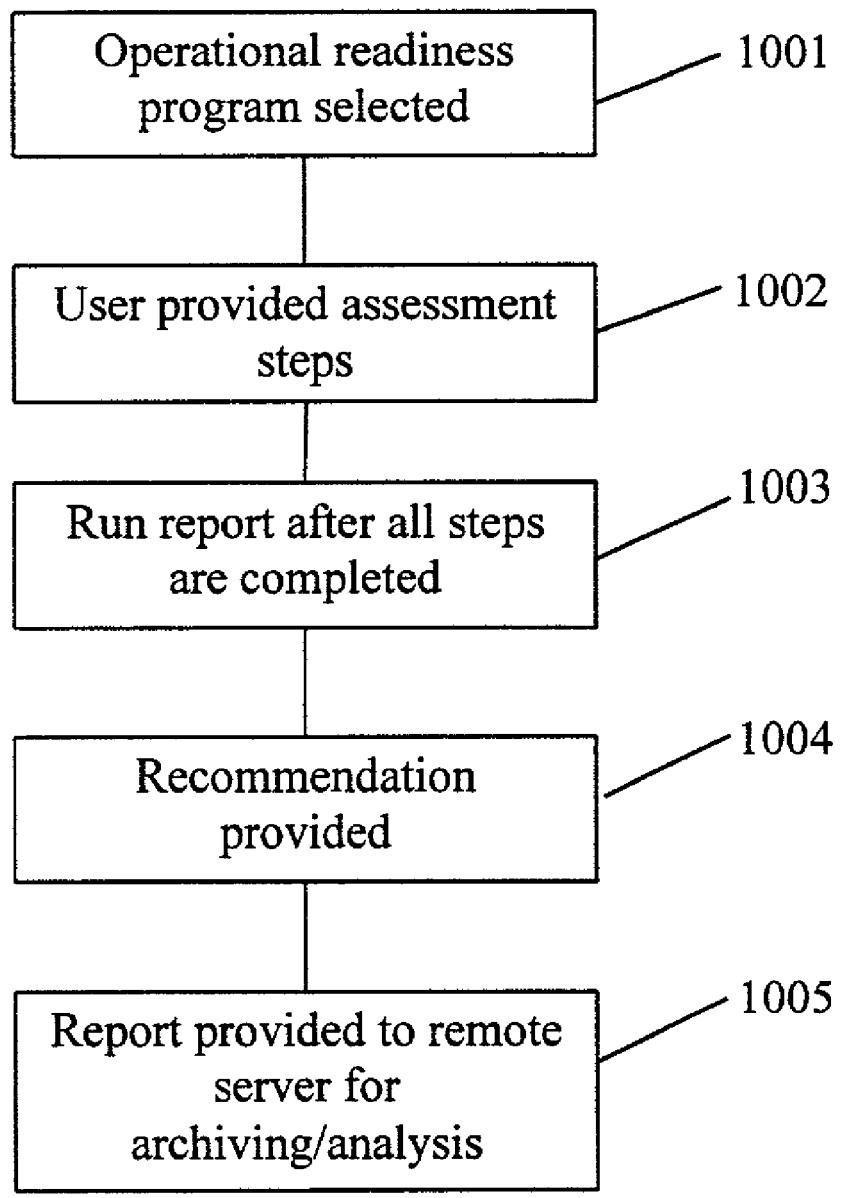
FIG. 10 illustrates a flow chart outlining a method relating to equipment readiness.

Referring to FIG. 10, a flow chart outlining a method relating to equipment readiness is described. An example relating to the airline industry will be used, but is not meant to be limiting. Airline pilots generally work through a manual checklist prior to the operation o aircraft. In accordance with the present invention, a pilot may utilize a program executed on a handheld device to be guided through an equipment readiness checklist. The operator (pilot) selects the operational readiness program associated with the equipment being check 1001. The program provides the operator with step-by-step instructions for checking the status of the equipment 1002. The checklist may be provided in the form of questions or statement (e.g., provide X gauge reading). Upon completion of the checklist, the user may run a report 1003 (or synchronized with a remote server for use by the system or monitors) describing the readiness (pass/fail) of the equipment. The report may include recommendations 1004 (e.g., troubleshooting criteria). Trouble shooting information together with a template of field test procedures may be provided to equipment technicians for repairing disorders. The report may be transmitted to a remote server 1005 for reporting/analysis. For example, the report (which preferably contains quantitative readings) may be synchronized with a black box located on an airplane. If there would ever be an issue as to whether equipment was properly checked out or if certain readings are indicative of causing equipment failures, the recorded information of the checklist would be useful in analyzing such issues.

Figure 11:
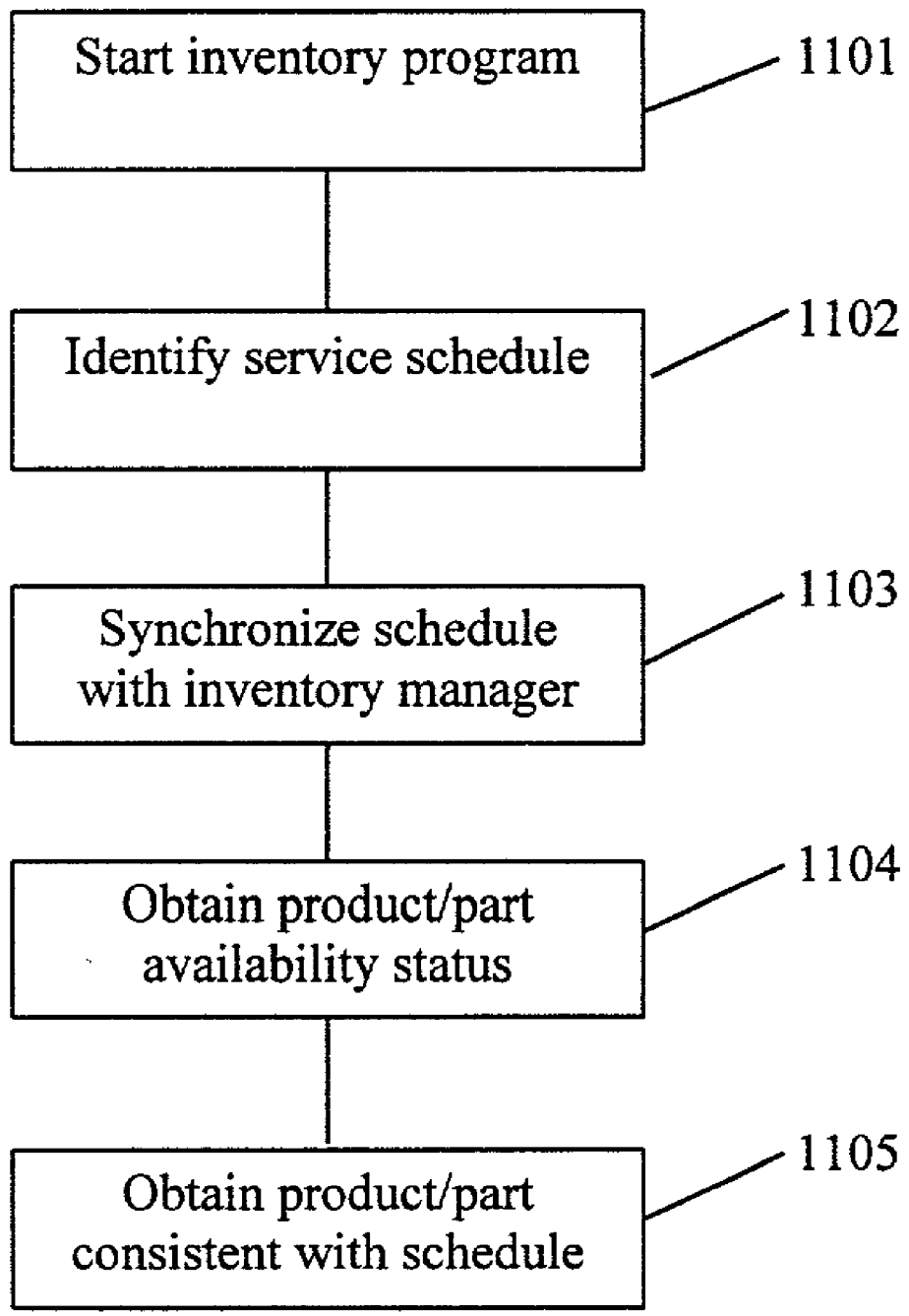
FIG. 11 illustrates a flow chart outlining a method relating to inventory tracking/ordering.

Referring to FIG. 11, a flow chart outlining a method relating to inventory tracking/ordering is described. Field technicians may utilize a handheld devices to ensure that the proper inventory will be provided prior to embarking on a daily service schedule. The assessor may start an inventory program 1101, identify a service schedule 1102, and synchronize the schedule 1103 with an inventory manager. The inventory manager assesses the schedule requirements and provides the technician with an inventory availability status 1104. The technician may coordinate inventory needs with the company automatically using this method so that no more inventory than is needed is taken to the field.

Figure 12:
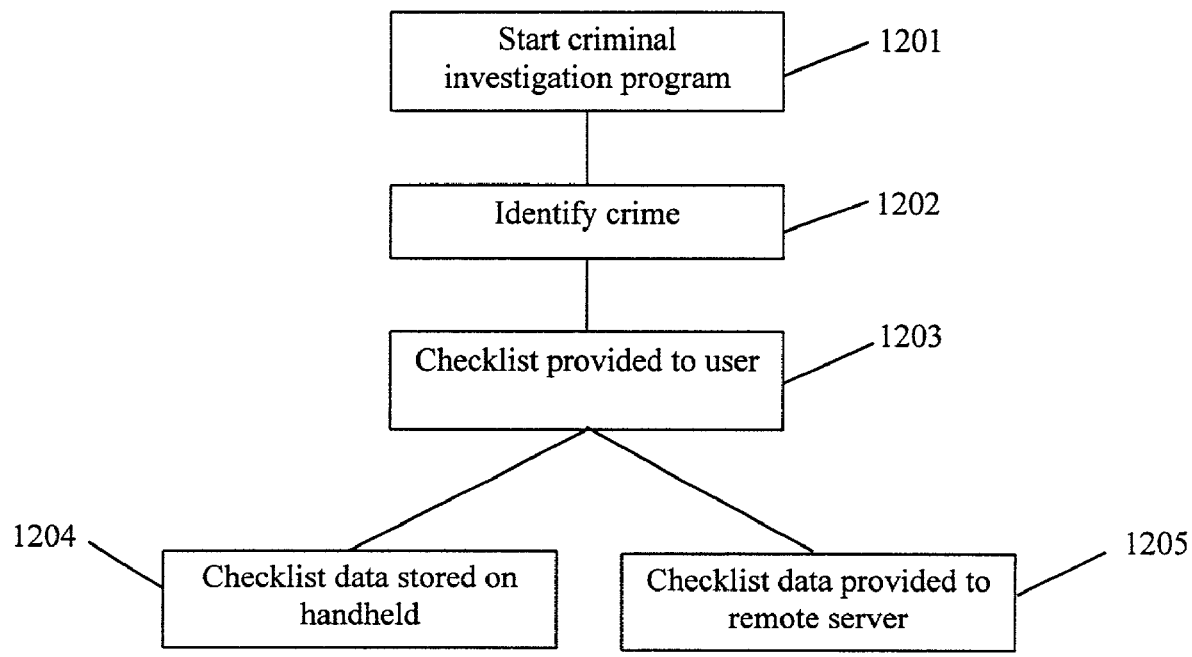
FIG. 12 illustrates a flow chart illustrating an assessment relating to criminal investigation.

Referring to FIG. 12, a flow chart illustrating an assessment relating to criminal investigation is described. Once the program opened 1201 on the handheld device, it may ask the assessor to identify the crime 1202. The assessor may then select the type of investigation being undertaken (e.g., crime scene, witness interviews, forensics, etc.). A checklist may be provided regarding the legal elements of a specific crime and exemplary evidence needed to prove the elements. The checklist and legal elements may be tailored to a particular legal jurisdiction. The investigator may complete a checklist by entering data relating to the investigation 1203. The checklist and/or data may be stored at the handheld 1204 for future reference, may be transmitted 1205 to a server for analysis (verification), and/or synchronized with computer for use in furtherance of an investigation. The ability to manage data from several investigators on large-scaled cases may be enhanced through the present invention, wherein comprehensive data form different sources may be analyzed, updated and reformatted for representation and distribution to plural case workers. Updated templates associated to a particular type of case may identify information shortfalls in a case.

Figure 13:
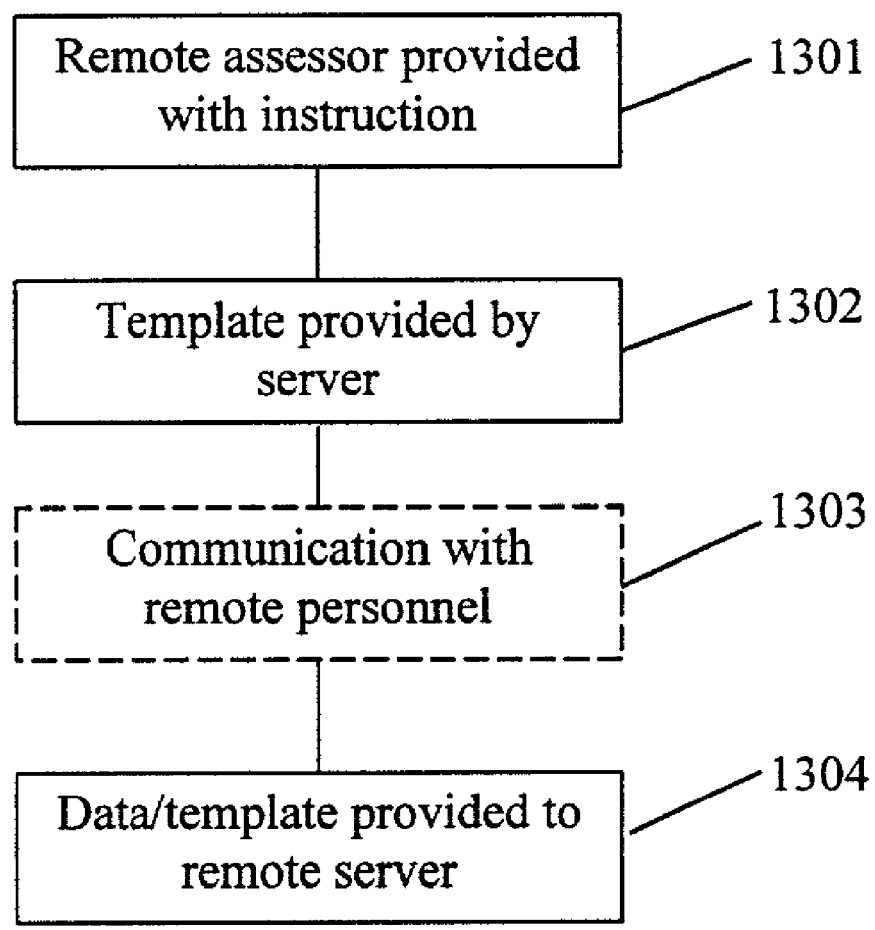
FIG. 13 illustrates a flow chart directed to multi-user functions in accordances with methods of the present invention.

Referring to FIG. 13, a flow chart directed to multi-user functions in accordance with the teaching of the present invention is provided. As an example to describe a multi-user field assessment, assume several field assessors/investigators are deployed to investigate and collect data over a broad area of land affected by an environmental catastrophe. Assessors equipped with handheld devices are assigned/deployed to specific positions of the affected environment. An assessor may first be provided initial instruction from a remote server 1301. Initial instructions may include summary information regarding the problem, required equipment, and Pinpoint directions to the assigned positions, which may be provided to assessors utilizing GPS. In cases where an assessor may already be deployed, the assessor may only be provided with initial information/instructions. At their respective positions, assessor are provide a template from the remote server 1302 comprising unique/updated instructions for their respective assessment of the position (e.g., data collection instructions). The template may operate in combination with programs resident in the handheld computer or may be accompanied by a computer program transmitted from the sever (e.g., in the form of a JAVA applet). During data collection, the assessor may communicate with remote support personnel 1303 utilizing communications means resident within the handheld device (e.g, chat). Procedural guidance may be provided through two-way communication with remote representatives. After the data has been collected in accordance with the template/programs, the data may be transmitted to the server 1304 wherein the data may be quickly and more accurately analyzed together with input from other assessors. In the case where initial GPS information was not provided to/or obtained from the assessor, GPS coordinates associated with the collected data may also be transmitted to the server with the collected data. The collected data and GPS coordinate associated with the collection of data would generally be the two most important attributes for the given scenario.

As will be appreciated by one of skill in the art, the present invention may be embodied as methods, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

Computer program code for carrying out operations of the present invention can be written in an object oriented programming language such as Java., Smalltalk or C++. The computer program code for carrying out operations of the present invention, however, may also be written in conventional procedural programming languages, such as the "C" programming language. The program code may execute entirely on the user's computer, as a stand-alone software package, or it may execute partly on the user's computer and partly on a remote computer. In the latter scenario, the remote computer may be connected to the user's computer through a LAN or a WAN, or the connection may be made to an external computer (for example, through the Internet using an Internet Service Provider). Personnel that may benefit from the assessment solutions provided herein include members of the construction, legal, medical, technical, hospitality, military and educational communities. The use of assessments as used herein is not meant to limit the invention. Examples of field assessments include, job estimates/bids, crime scene investigations, medical procedures, daily punch/task list management, equipment/system testing/troubleshooting, and third-party status/feedback collection. Accomplishment of an assessments may includes methods for guided, interactive data collection by handheld computing device users, and storage and/or transmission of collected data for computer analysis. Data, once analyzed by a computer, may result in a complete assessment of or a request for additional data collection by the user.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A handheld data management device for field assessments, comprising:
   a memory for storing field assessment programs and related data;
   a microprocessor for executing field assessment programs;
   a field assessment program stored within said memory and including at least one template and instructions for a handheld field assessment device user to carry out at least one of: construction industry project analysis, HVAC system analysis, project management, equipment readiness, system and equipment troubleshooting, remote inventory tracking and ordering, conducting legal investigations in the field, and multi-user remote function coordination;
   a user interface adapted for enabling the handheld field assessment device user to interact with said field assessment program; and
   sychronization means for providing data to and retrieving data from remote computing resources.

2. The handheld data management device of claim 1, further comprising a positioning module, for providing handheld device location identification.

3. The device of claim 1, further comprising a wireless communication module for providing access to data from remote resources to said device.

4. The handheld data management device of claim 1, further comprising a positioning module, for providing handheld device location identification.

5. The device of claim 4, further comprising a wireless communication module for providing access to data from remote resources to said device.

6. The device of claim 1, further comprising a wireless communication module for providing access to data from remote resources to said device.

7. The handheld data management device of claim 6, further comprising a positioning module, for providing handheld device location identification.

8. A handheld field assessment device, comprising:
   a field assessment program module for providing guidance to user handheld field assessment device user, and for analyzing input data associated with the field assessment, said field assessment program module including instructions for the handheld field assessment device user to carry out at least one of: construction industry project analysis, HVAC system analysis, project management; equipment readiness, system and equipment troubleshooting, remote inventory tracking and ordering, conducting legal investigations in the field, and multi-users remote function coordination;
   a positioning module, for providing handheld device location identification; and
   a wireless communication module for providing access to remote data resources to said device.

9. A method of conducting a field assessment using a handheld data management device, comprising:
   providing a hand held data management device user performing as a field assessor access to a industry-specific field assessment program module for enabling the field assessor to execute at least one of the following field assessments: construction industry project analysis, HVAC system analysis; project management, equipment readiness, system and equipment troubleshooting, remote inventory tracking and ordering, conducting legal investigations in the field, and multi-users remote function coordination;
   executing said program module to conduct the field assessment;
   providing field-specific information required by said program module for said program module to render data in support of said field assessment; and
   retrieving data through said handheld data management device in support of said field assessment.

10. The method of claim 9, further comprising:
    providing data to a remote resource for analysis;
    retrieving enhanced data from said remote resource for use in conducting the field assessment.

11. The method of claim 10, wherein data provided to a remote resource is a query message from a field assessor to a remote counselor and enhanced data from said remote resource is a response message provided by said remote counselor in response to said query message.

12. The method of claim 11, wherein said response message includes supporting data files.

13. The method of claim 9, further comprising accessing a remote data resource for retrieving data in support of said assessment.

14. The method of claim 13 wherein said data resource is a third party database accessible over the Internet.

15. The method of claim 9, further comprising:
    providing two-way communication between remote computing means and handheld data management devices to facilitate real-time access to remote programs, assistance and/or information related to the field assessment being undertaken by using a handheld data management device user.

16. The method of claim 15, wherein data is provided to said remote resource in the form of a query message from a field assessor to a remote counselor and enhanced data from said remote resource is a response message provided by said remote counselor in response to said query message.

17. The method of claim 16, wherein said response message includes supporting data files.

18. The method of claim 9, further comprising:
    accessing a remote data resource for retrieving data in support of said assessment.

19. The method of claim 18 wherein said data resource is a third party database accessible over the Internet.

20. The method of claim 9, further comprising:
providing data to a remote resource for analysis;
retrieving enhanced data from said remote resource for use in conducting the field assessment.

21. The method of claim 20, wherein data provided to a remote resource is a query message from a field assessor to a remote counselor and enhanced data from said remote resource is a response message provided by said remote counselor in response to said query message.

22. The method of claim 21, wherein said response message includes supporting data files.

23. The method of claim 9, further comprising:
accessing a remote data resource for retrieving data in support of said assessment.

24. The method of claim 23 wherein said data resource is a third party database accessible over the Internet.

25. The method of claim 9, further comprising:
providing two-way communication between remote computing means and handheld data management devices to facilitate real-time access to remote programs, assistance and/or information related to the field assessment being undertaken by using a handheld data management device user.

26. The method of claim 25, wherein data is provided to said remote resource in the form of a query message from a field assessor to a remote counselor and enhanced data from said remote resource is a response message provided by said remote counselor in response to said query message.

27. The method of claim 26, wherein said response message includes supporting data files.

28. A method of conducting an assessment of a field problem by an assessor utilizing a handheld data management device, comprising:
obtaining direction to a field problem to conduct a field assessment for at least one of: construction industry project analysis, HVAC system analysis; project management, equipment readiness, system and equipment troubleshooting, remote inventory tracking and ordering, conducting legal investigations in the field, and multi-users remote function coordination using positioning and navigation means provided through said handheld data management device;
starting an assessment program associated with the field problem;
providing specific information required by the assessment program and related to the field problem;
analysis of said specific information by said handheld data management device; and
rendering output by said handheld data management device for use in support of said field problem.

29. The method of claim 28, further comprising identifying the field problem by providing information of at least one of customer identity, problem location, assessment date.

30. The method of claim 28, wherein if said problem is a construction appraisal said method further comprises providing information of at least one of customer identity, problem location, assessment date, project start date.

31. A method utilizing a handheld data management device for remote inventory management, comprising:
starting an inventory program from a handheld data management device, said program used to ensure that the proper inventory will be provided to the handheld data management device user prior to the user undertaking a daily field service schedule;
enabling the user to identifying service schedule requirements;
enabling the user to synchronize the schedule with inventory data stored in a server wirelessly accessible by said handheld data management device;
said handheld management device adapted to conduct in cooperation with the server an assessment of service schedule requirements and available inventory; and
providing the user with inventory availability status through the handheld data management device that is based on inventory needs identified in said service schedule.

32. The method of claim 31 wherein inventory needed and available for said service schedule are reserved through said program and said server to an inventory supplier, wherein needed inventory is available to the user for scheduled service calls.

* * * * *